United States Patent
Robins et al.

(10) Patent No.: US 6,264,960 B1
(45) Date of Patent: *Jul. 24, 2001

(54) TREATMENT OF VASCULAR EVENTS USING LIPID-MODIFYING COMPOSITIONS

(76) Inventors: Sander J. Robins, 86 Framingham Rd., Southboro, MA (US) 01772; Hanna Bloomfield Rubins, 4101 Sunset Blvd., St. Louis Park, Minneapolis, MN (US) 55416; Dorothea Collins, 541 Nut Plains Rd., Guilford, CT (US) 06437

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/189,699

(22) Filed: Nov. 10, 1998

(51) Int. Cl.[7] .............................. A61K 9/00; A61K 31/19; A61K 31/21

(52) U.S. Cl. ................. 424/400; 424/422; 424/434; 424/436; 514/568; 514/506; 514/510; 514/569; 514/570; 514/824

(58) Field of Search ......................... 424/400, 422, 424/434, 436, 43; 514/568, 506, 510, 569, 570, 824

(56) References Cited

U.S. PATENT DOCUMENTS

| | | | |
|---|---|---|---|
| 3,674,836 | 7/1972 | Creger | 260/473 |
| 4,250,191 | 2/1981 | Edwards | 424/308 |
| 4,788,183 | 11/1988 | Darrow | 514/166 |
| 4,891,220 | 1/1990 | Donzis | 424/88 |
| 4,933,165 | 6/1990 | Brown | 424/10 |
| 5,173,287 | 12/1992 | Smith | 424/10 |
| 5,211,947 | 5/1993 | Brannan et al. | 424/94.63 |
| 5,312,814 | 5/1994 | Biller et al. | 514/39 |
| 5,470,845 | 11/1995 | Magnin et al. | 514/121 |
| 5,530,145 | 6/1996 | Wang et al. | 549/328 |
| 5,593,971 | 1/1997 | Tschollar et al. | 514/39 |

FOREIGN PATENT DOCUMENTS

| | | |
|---|---|---|
| 757911 | 2/1997 | (EP) . |
| 793958 | 9/1997 | (EP) . |
| WO 97/35576 | 10/1997 | (WO) . |
| WO 98/03069 | 1/1998 | (WO) . |

OTHER PUBLICATIONS

Rubins, M.D., H.B., et al., "Gemfibrozil for the Secondary Prevention of Coronary Heart Disease in Men with Low Levels of High–Density Lipoprotein Cholesterol," *The New England Journal of Medicine,* 341: 410–418 (1999).

Rubins, H.B., et al., "Rationale and design of the Department of Veterans Affairs High–Denisty Lipoprotein Cholesterol Intervention Trial (HIT) for secondary prevention of coronary artery disease in men with low high–density lipoprotein cholesterol and desirable low–density lipoprotein cholesterol," *Am. J. Cardiol.* 71(1): 45–52 (1993).

Fauci et al. "Harrison's Principles of Internal Medicine, 14th Ed.", McGraw–Hill, Inc., New York, 2146–2148 (1998).

Rubenfire, et al. "Treatment Strategies for Management of Serum Lipids: Lessons Learned From Lipid Metabolism, Recent Clinical Trials, and Experience With the HMG CoA Reductase Inhibitors," Progress in Cardiovascular Diseases, 41(2), pp 95–116 (1998).

Wood et al., "Prevention of Coronary Heart Disease in Clinical Practice," European Society of Cardiology, European Atherosclerosis Society, European Society of Hypertension, International Society of Behavioural Medicine, European Society of General Practice/Family Medicine, European Heart Network. Atherosclerosis, 140, #2, pp. 199–270, 1998.

Belalcazar, et al., "Defining Specific Goals of Therapy in Treating Dyslipidemia in the Patient With Low High–Density Lipoprotein Cholesterol," Progress in Cardiovascular Diseases, 41(2), pp 151–174 (1998).

National Cholesterol Education Program ("NCEP"), "Fibric Acid Derivatives" pp. III–10 and III–11., 1993.

*Primary Examiner*—Gollamudi S. Kishore
(74) *Attorney, Agent, or Firm*—Hamilton, Brook, Smith & Reynolds, P.C.

(57) ABSTRACT

The claimed invention pertains to methods for treating a patient who is at risk for a vascular (e.g., cardiovascular, cerebrovascular) event comprising administering to the patient an effective amount of a lipid-modifying drug. The claimed methods are particularly effective in patients having a lipid profile comprising a low Low Density Lipoprotein and a low High Density Lipoprotein.

6 Claims, No Drawings

TREATMENT OF VASCULAR EVENTS USING LIPID-MODIFYING COMPOSITIONS

BACKGROUND OF THE INVENTION

Vascular disorders, including heart disease and stroke, persist as a leading cause of death in certain age and ethnic groups. A need exists, therefore, for improved treatments for patients at risk for vascular disorders. In particular, a need exists to reduce the occurrence and/or severity of vascular disorders.

SUMMARY OF THE INVENTION

The invention pertains to methods for treating a patient who is at risk for a vascular event (e.g., cardiovascular or cerebrovascular event) comprising administering to the patient an effective amount of a lipid or cholesterol modifying drug. In particular, the patient is one having a lipid profile with a low High Density Lipoprotein-Cholesterol (HDL-C) and a low Low Density Lipoprotein-Cholesterol (LDL-C). A low HDL-C is less than about 40 mg/dL, and a low LDL-C is less than about 130 mg/dL.

The lipid/cholesterol modifying drug comprises a fibric acid or derivative thereof. Examples of fibric acid or derivatives thereof include gemfibrozil, fenofibrate, bezafibrate, ciprofibrate, clofibrate, clinofibrate, niacin and/or combinations thereof.

The claimed method implicates the treatment of various vascular events that can be characterized by a clot in the vessel (e.g., artery, vein) or narrowing of the vessel. A clot which forms in a vessel can partially or fully block blood flow. Examples of such diseases are a thrombotic disorder, myocardial infarction, angina, stroke, pulmonary embolism, transient ischemic attack, deep vein thrombosis, thrombotic re-occlusion subsequent to a coronary intervention procedure and a disorder in which at least one major coronary artery exhibits greater than 50% stenosis. The treatment reduces the occurrence and/or severity of these vascular events.

The claimed methods result in at least a 10% (e.g., 15% or 20%) reduction of the patient's triglyceride level, and/or at least a 5% (e.g., 7% or 10%) increase in the level of HDL-C.

The claimed invention also embodies methods for preventing a cardiovascular and/or cerebrovascular event in an individual who has a lipid profile comprising a low HDL-C level and a low LDL-C level, comprising administering an effective amount of fibric acid or derivative thereof in a carrier (e.g., a pharmaceutically acceptable carrier). The individual can also be at risk for a cardiovascular and/or cerebrovascular event.

Advantages of the claimed invention include the ability to treat cardiovascular and/or cerebrovascular events with lipid modifying drugs/compositions, especially in patients who already have a low HDL-C and low LDL-C lipid profile. The claimed methods provide an effective way to treat, prevent, and/or reduce the reoccurrence or severity of these cardiovascular and/or cerebrovascular events.

DETAILED DESCRIPTION OF THE INVENTION

The claimed invention relates to methods for treating a patient who is at risk for a vascular event (e.g., cardiovascular and/or cerebrovascular event), comprising administering an effective amount of a lipid/cholesterol-modifying drug. These patients can also have a lipid profile with a low High Density Lipoprotein-Cholesterol (HDL-C) and a low Low Density Lipoprotein-Cholesterol (LDL-C).

As defined herein a vascular event refers to a disease or disorder of a blood vessel and/or circulation of, for example, the heart (e.g., cardiovascular event) or brain (e.g., cerebrovascular event). A cardiovascular and/or cerebrovascular event can be a thrombotic disorder. A thrombotic disorder/event occurs, for example, when a clot forms and lodges within a blood vessel. The blockage may fully block or partially block the blood vessel causing a thrombotic disorder. Other examples of cardiovascular and/or cerebrovascular events include a narrowing or constriction of a blood vessel, myocardial infarction (MI), angina, stroke, pulmonary embolism, transient ischemic attack (TIA), deep vein thrombosis, thrombotic re-occlusion subsequent to a coronary intervention procedure or disorders in which at least one major coronary artery exhibits greater than 50% stenosis. Two phases of a cardiovascular and/or cerebrovascular event may exist, an ischemic stage and a necrotic stage. A patient may suffer from ischemia in which a decrease of blood flow may occur. This decrease in blood flow causes a decrease in tissue oxygenation. After prolonged ischemia, the tissue may undergo necrosis which is death of the tissue. Therefore, patients who are at risk for a cardiovascular and/or cerebrovascular event may exhibit elevated levels of ischemic markers and/or necrosis markers.

Patients who are at risk for a cardiovascular and/or cerebrovascular event are patients who manifest at least one symptom indicative of a vascular disorder/event. Symptoms that are indicative of a coronary-related vascular event, for example, include chest pain, abnormal electrocardiograms, elevated levels of ischemic markers, necrosis markers, or thrombin/fibrin generation markers. Such markers include, but are not limited to, Creatine Kinase with Muscle and/or Brain subunits (CKMB), D-Dimer, F1.2, thrombin antithrombin (TAT), soluble fibrin monomer (SFM), fibrin peptide A (FPA), myoglobin, thrombin precursor protein (TPP), platelet monocyte aggregate (PMA) and troponin. Patients who are at risk also include patients having a history of a thrombotic event (e.g. disorder), including Coronary Heart Disease (CHD), stroke, or TIAs. A history of CHD can include, for example, a history of MI, coronary revascularization procedure, angina with ischemic changes, or a positive coronary angiogram (e.g., showing greater than about 50% stenosis of at least one major coronary artery).

In particular, the claimed invention involves patients who are at risk for a cardiovascular and/or cerebrovascular event and have a low HDL-C and low LDL-C lipid profile. A low HDL-C is less than about 40 mg/dL, and a low LDL-C is less than about 130 mg/dL. Lipoproteins are complexes which contain both a lipid and protein. Most of the lipids in plasma are present as lipoproteins and are transported as such. Lipoproteins are characterized by their flotation constants (e.g., densities). Various classes of lipoproteins exist and include HDLs and LDLs. LDLs are particularly rich in cholesterol esters. The methods also include patients who have a triglyceride level of less than about 320 mg/dL (e.g., less than about 310 or 300 mg/dL).

Assessment of these levels are associated with assessing the risk of cardiovascular and/or cerebrovascular disease. Traditionally, high levels of LDL and/or low levels of HDL are associated with coronary artery disease. However, the correlation between these levels and vascular events does not always occur. In fact, in a study performed, 25% of the patients who were at risk for a cardiovascular and/or cerebrovascular event exhibited low HDL and low LDL levels. In this study, patients at risk were documented by a history of past MI, coronary revascularization procedure, angina with ischemic changes, or a positive coronary angiogram showing greater than 50% stenosis of at least one major coronary artery. These patients also exhibited a lipid profile characterized by a low HDL-C (less than 40 mg/dL) and a low LDL-C (less than 130 mg/dL) based on the entrance lipid criteria for the population enrolled in the studied, as well as the mean baseline for the population. These patients also had a triglyceride level of about less than 300 mg/dL.

Lipoproteins levels and triglyceride levels are measured and assessed using routine methods known in the art. Commercially available kits and assays may be used to evaluate the level of HDL-C, LDL-C and level of triglyceride.

Administering a lipid modifying drug (e.g., fibric acid or derivative thereof) in an effective amount results in a reduction of recurrent cardiovascular and/or cerebrovascular events. Use of the methods described herein results in a reduction of at least about 10% (e.g., 15%, 20%, 25%) in the number of recurrent heart attacks, cardiac deaths and/or strokes. Administering a lipid modifying drug in a patient with low HDLC and low LDL-C levels also results in an increase of the HDL-C level and/or reduction of the triglyceride level in a patient. In particular, use of the methods described herein results in an increase of about at least 5% (e.g., 7% or 10%) of HDL-C level, and/or a reduction in the triglyceride level by at least about 10% (e.g., 15% or 20%).

The claimed methods also relates to method for reducing the occurrence of a cardiovascular and/or cerebrovascular event in a patient who is at risk for such a disorder. Reducing the occurrence of a cardiovascular and/or cerebrovascular disorder refers to reducing the probability that a patient will develop a cardiovascular and/or cerebrovascular disorder, or delaying the onset of the disorder. Reducing the severity of a cardiovascular and/or cerebrovascular disorder refers to a reduction in the degree of at least one symptom of the disorder. The claimed invention embodies methods for preventing the onset of a cardiovascular and/or cerebrovascular disorder in an individual having a low HDL-C and low LDL-C, comprising administering a lipid modifying drug. The individual can be at risk for developing a cardiovascular and/or cerebrovascular disorder, as demonstrated by exhibiting at least one symptom of a cardiovascular and/or cerebrovascular disorder or having a history of a cardiovascular and/or cerebrovascular disorder, as described herein.

Lipid Modifying Drugs, Fibric Acid and Derivatives Thereof

A lipid modifying drug refers to a drug (e.g., composition) that can influence the lipoprotein levels. In particular, a lipid modifying drug refers to a drug which can increase the level of HDL-C and reduce the triglyceride level. The claimed invention further relates to administering drugs that are now known, and developed in the future. Many of these drugs are known and commercially available. Well recognized lipid modifying drugs are fibric acid or fibric acid derivatives. Examples of such compositions are gemfibrozil, fenofibrate, bezafibrate, ciprofibrate, clofibrate, clinofibrate and niacin. These drugs are commercially available, and can also be made using methods known in the art. A lipid-modifying drug and its dosages and modes of administration are described in U.S. Pat. No. 4,788,183, the teachings of which are incorporated herein by reference in their entirety.

Niacin refers to 3-pyridinecarboxylic acid, and to equivalent compounds which are converted to 3-pyridinecarboxylic acid in vivo. Fenofibrate is also commercially available, and methods for making it are known. (WO 9803069, WO 9735576, EP 793958, EP 757911, the teachings of which are incorporated herein by reference in their entirety.)

Gemfibrozil refers to 5-(2,5-dimethylphenoxy)-2,2-dimethylpentanoic acid, and its pharmaceutically acceptable salts and esters. Gemfibrozil is commercially available under the trademark LOPID® from Parke, Davis & Company, Detroit Mich., and can be prepared by the methods disclosed in U.S. Pat. No. 3,674,836, the teachings of which are incorporated herein by reference in their entirety. There are several reported syntheses of gemfibrozil and certain analogues. For example, U.S. Pat. No. 3,674,836 (1972) discloses gemfibrozil and its analogues thereof, as well as a process for preparing them, the teachings of which are incorporated herein by reference in their entirety. U.S. Pat. No. 3,707,566 (1987) discloses a process for preparing gemfibrozil, and methods of making cholesterol modifying compounds are described in U.S. Pat. No. 5,530,145, the teachings of which are incorporated herein by reference in their entirety.

Administration and Dosages.

The terms "pharmaceutically acceptable carrier" or a "carrier" refer to any generally acceptable excipient or drug delivery device that is relatively inert and nontoxic. A preferred embodiment is to administer the lipid modifying drug orally, (e.g., tablet or capsule form). Exemplary carriers include calcium carbonate, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17th Ed., Mack Pub. Co., Easton, Pa.), the teachings of which are incorporated herein by reference in their entirety.

Suitable carriers (e.g., pharmaceutical carriers) also include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. Such preparations can be sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation. A carrier (e.g., a pharmaceutically acceptable carrier) is preferred, but not necessary to administer a lipid modifying drug. For parenteral application, particularly suitable are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-polyoxypropylene block polymers, and the like. Ampules are convenient unit dosages.

The lipid-modifying (e.g., lipid modulating) compositions of the present invention can be administered intravenously, parenterally, orally, nasally, by inhalation, by implant, by injection, or by suppository. A preferred method of administration is orally. The composition can be administered in a single dose or in more than one dose over a period of time to confer the desired effect.

The actual effective amounts of lipid modifying drug can vary according to the specific drug being utilized, the particular composition formulated, the mode of administration and the age, weight and condition of the patient, for example. As used herein, an effective amount of a lipid-modulating drug is an amount of the drug which is capable of increasing the level of HDL-C and/or reducing the triglyceride level. Dosages for a particular patient can be determined by one of ordinary skill in the art using conventional considerations, (e.g. by means of in appropriate, conventional pharmacological protocol). As described herein, a daily oral dose for a male patient of gemfibrozil, for example, is about 800–1300 mg/day, and preferably between 900–1200 mg/day.

EXEMPLIFICATION

This study, the Veterans Administration HDL Intervention Trial (VA-HIT), is a seven year, 30 center, randomized, placebo controlled, double blind secondary prevention trial designed to determine if fibric acid (e.g., gemfibrozil) reduces the incidence of myocardial infarction (MI) and CHD death in male CHD patients who have low levels of both HDL-C and LDL-C. Power calculations indicated that a sample size of 2500 would yield 90% power to detect a 20% difference between the treatment groups for the primary endpoint (time to MI or CHD death) using a two-tailed alpha of 0.05 in an intention to treat analysis assuming a cumulative event rate in the placebo group of 30%. Primary endpoints and the secondary endpoint, stroke, were adjudicated by blinded committees using standard criteria. Gemfibrozil (1200 mg/day, orally) was selected with the goal of raising HDL-C and lowering triglycerides (TG) without affecting LDL-C.

The study included men with known coronary heart disease (CHD) as documented by a history of past myocardial infarction (MI), coronary revascularization procedure, angina with ischemic changes, or a positive coronary angiogram (showing>50% stenosis of at least one major coronary artery) and a fasting plasma (or serum) lipid profile characterized by a low high-density lipoprotein (HDL)-cholesterol as well as a low Low-Density lipoprotein (LDL)-cholesterol. A significant reduction of new or recurrent CHD events (including nonfatal MI, CHD death, as well as certain forms of stroke or TIA) occurred by treatment with gemfibrozil at a standard daily dose of 1200 mg/day (in the USA).

"Low HDL-C" was defined as less than 40 mg/dL and "low LDL-C" was defined as less than 130 mg/dL values which are based on the entrance lipid criteria for the population enrolled in VA-HIT as well as the mean baseline HDL-C and LDL-C values of the VA-HIT population.

Other fibric acid derivatives that are structurally similar to gemfibrozil including but not limited to 1) fenofibrate, 2) bezafibrate, and 3) ciprofibrate have a similar significant clinical benefit as gemfibrozil when used to treat patients belonging to this subpopulation.

The benefits observed in this study were seen in following subgroups:
1) Patients who were young as well as old (>65 years)
2) diabetics as well as non-diabetics
3) patients with lower values of triglycerides (<161 mg/dL) as well as higher (from 161 to 300 mg/dL) values.

A clinical benefit has been shown in CHD patients who do not have a high (total) or high HDL-C by treating them with a particular lipid-modifying drug.

2531 patients were enrolled and followed for a median of 5 years. Compliance, lipid changes, endpoints rates, losses to follow-up, and crossovers to active treatment have been consistent with the original projections. At baseline, the mean age was 64 yrs; average lipid values were, in mg/dL: HDL-C 32; TG 161; LDL-C 111; total cholesterol 176. (For comparison, the mean baseline LDL-C in recent major secondary prevention trials was 189 in the Scandinavian Simvastatin Survival Study, 139 in the Cholesterol and Recurrent Events study, and 150 in the Long-Term Intervention with Pravastatin in Ischemic Disease study). The mean body mass index was 29±5. The prevalence of diabetes was 25% and of hypertension 57%. Aspirin and beta blockers were used by 82%, and 43% of patients, respectively.

Many heart disease patients have LDL cholesterol that is not high or even average. These patients often have low levels of the good cholesterol, HDL, as their primary lipid abnormality. Overall, approximately 24% of people with CHD, or about 3 million people in the United States, have this lipid profile (low LDL and low HDL).

VA-HIT was a major clinical trial to investigate whether lipid therapy benefits people with heart disease whose primary lipid abnormality is a low level of HDL. The VA-HIT study enrolled 2531 male veterans with heart disease who had low levels of LDL cholesterol and low levels of HDL cholesterol. The average LDL level was 111 mg/dL and HDL was 32 mg/dL. Patients were randomly assigned to receive either gemfibrozil or a placebo. Gemfibrozil, a fibric acid, significantly raised HDL and lowered triglycerides, another blood fat that may contribute to heart disease. Gemfibrozil did not lower LDL cholesterol.

Data:
2531 men with CHD enrolled in trial 1991-1993. The trial ended Jul. 31, 1998 with median follow-up of 5.1 years. Vital status of patients known is 99.2%. 71% remained on assigned therapy at end of trial which is about the average in a long trial.

| Percent change in Lipids | | |
|---|---|---|
| | PLACEBO | GEMFIBROZIL |
| *total cholesterol | +2.1 | −2.9 |
| LDL-C | +4.0 | +3.6 |
| *HDL-C | +1.8 | +7.5 |
| *Triglycerides | +9.6 | −24.5 |

*Statically significant differences

| Primary Endpoints: | | | |
|---|---|---|---|
| | PLACEBO | GEMFIBROZIL | RELATIVE RISK REDUCTION |
| CHD death/ nonfatal MI | 22% | 17% | 22% |

| Other Endpoints which were significantly benefitted by Gemfibrozil: | | |
| --- | --- | --- |
| | INCIDENCE RATE | |
| | PLACEBO | GEMFIBROZIL |
| transient ischemia attack (TIA) | 4.2% | 1.7% |
| carotid endarterectomy | 3.5% | 1.3% |
| total reported stroke | 7.0% | 5.0% |
| hospitalization for congestive heart failure | 13.3% | 10.6% |

The benefit achieved in VA-HIT with gemfibrozil in reducing major CHD events in U.S.A. patients without an increased LDL-C was at least as great as with reductase inhibitors (e.g., statins) in reducing CHD endpoints in the patients with a high LDL-C.

The major findings of this seven year study were that:

Patients receiving gemfibrozil had a 22% reduction in the number of heart attacks and cardiac deaths, the primary study endpoint. This finding was highly statistically significant (p=0.0063).

Using the combined endpoint of heart attacks, cardiac deaths, and strokes patients receiving gemfibrozil had a 24% reduction in these major events (p=0.0011).

Gemfibrozil was effective in both diabetics and non-diabetics and in younger as well as older patients.

Gemfibrozil was not associated with any major adverse events. Major adverse events that were monitored included deaths from any cause and cancer.

VA-HIT data indicates that 18 patients would need to be treated with gemfibrozil over a time period (e.g., between 1 and 5 years) to prevent one heart attack, cardiac death, or stroke. VA-HIT study also provides direct clinical trial evidence of a beneficial effect of lipid therapy in CHD patients with low HDL-cholesterol and low LDL-cholesterol. This study demonstrates a clinical benefit from raising HDL-cholesterol and lowering triglycerides without lowering LDL-cholesterol.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for treating a human having a lipid profile of a HDL-C level of less than about 40 mg/dL prior to treatment, and a LDL-C level of less than about 130 mg/dL prior to treatment, wherein the human is at risk for a cardiovascular or cerebrovascular event, comprising administering to the human an effective amount of a fibric acid of derivative thereof in a pharmaceutically acceptable carrier, wherein the fibric acid or derivative thereof is selected from a group consisting of: gemfibrozil, fenofibrate, bezafibrate, ciprofibrate, clofibrate and clinofibrate; the cardiovascular or cerebrovascular event is selected from a group consisting of: thrombotic disorder, myocardial infarction, angina, stroke, transient ischemic attack, thrombotic re-occlusion subsequent to a coronary intervention procedure and a disorder in which at least one major coronary artery exhibits greater than 50% stenosis; and wherein an increase of HDL-C occurs after treatment.

2. The method of claim 1, wherein a reduction of the occurrence or severity of the vascular event occurs.

3. The method of claim 1, wherein the triglyceride level is reduced by a least about 10% after treatment.

4. The method of claim 3, wherein the triglyceride level is reduced by at least about 20%.

5. The method of claim 1, wherein the HDL-C level is increased by at least about 5% after treatment.

6. The method of claim 5, wherein the HDL-C level is increased by at least about 7%.

* * * * *